(12) United States Patent
Ouchi et al.

(10) Patent No.: US 8,698,085 B2
(45) Date of Patent: Apr. 15, 2014

(54) ANALYSIS APPARATUS

(75) Inventors: Toshihiko Ouchi, Machida (JP); Toshihiko Takeda, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 254 days.

(21) Appl. No.: 13/124,122

(22) PCT Filed: Dec. 18, 2009

(86) PCT No.: PCT/JP2009/071720
§ 371 (c)(1),
(2), (4) Date: Apr. 13, 2011

(87) PCT Pub. No.: WO2010/074280
PCT Pub. Date: Jul. 1, 2010

(65) Prior Publication Data
US 2011/0198501 A1    Aug. 18, 2011

(30) Foreign Application Priority Data

Dec. 25, 2008 (JP) .................................. 2008-331601
Nov. 20, 2009 (JP) .................................. 2009-265226

(51) Int. Cl.
*G01J 5/02* (2006.01)

(52) U.S. Cl.
USPC ........................................................ 250/343

(58) Field of Classification Search
CPC .......... G01N 21/3504; G01N 21/3581; G01N 33/497; G01J 5/02; A61B 5/14551; A61B 2010/0083
USPC ........................................................ 250/343
See application file for complete search history.

(56) References Cited

U.S. PATENT DOCUMENTS

| | | | |
|---|---|---|---|
| 3,174,037 A | | 3/1965 | Demorest et al. |
| 4,041,932 A | * | 8/1977 | Fostick .................. 600/326 |
| 4,446,869 A | * | 5/1984 | Knodle .................. 600/529 |
| RE31,879 E | * | 5/1985 | Lubbers et al. ............ 436/133 |
| 4,709,150 A | * | 11/1987 | Burough et al. .......... 250/338.1 |
| 4,956,578 A | | 9/1990 | Shimizu et al. |

(Continued)

FOREIGN PATENT DOCUMENTS

| | | |
|---|---|---|
| JP | 2005-147962 | 6/2005 |
| JP | 2005-147962 A | 6/2005 |

(Continued)

OTHER PUBLICATIONS

U.S. Appl. No. 13/093,804, filed Apr. 25, 2011. Applicant: Toshihiko Ouchi, et al.

(Continued)

*Primary Examiner* — Marcus Taningco
(74) *Attorney, Agent, or Firm* — Fitzpatrick, Cella, Harper & Scinto (57) ABSTRACT

An analysis apparatus for analyzing a gas by a terahertz wave or an infrared ray comprises a generator for generating the terahertz wave or the infrared ray; a trapping unit having a trapping film for trapping a gas and being placed to be capable of causing interaction between the gas trapped by the trapping film and the terahertz wave or infrared ray generated by the generator; and a detector for detecting the interaction of the gas with the terahertz wave or infrared ray; wherein the trapping unit comprises a structure for contact with a site evolving the gas; and the structure holds the trapping film separately from the site.

7 Claims, 5 Drawing Sheets

(56) References Cited

U.S. PATENT DOCUMENTS

| | | | | |
|---|---|---|---|---|
| 5,023,110 | A | 6/1991 | Nomura et al. | |
| 5,155,416 | A | 10/1992 | Suzuki et al. | |
| 5,239,576 | A | 8/1993 | Yoshida et al. | |
| 5,285,129 | A | 2/1994 | Takeda et al. | |
| 5,391,871 | A | 2/1995 | Matsuda et al. | |
| 5,470,265 | A | 11/1995 | Nomura et al. | |
| 5,576,051 | A | 11/1996 | Takeda et al. | |
| 5,578,897 | A | 11/1996 | Nomura et al. | |
| 5,586,131 | A | 12/1996 | Ono et al. | |
| 5,593,899 | A * | 1/1997 | Wilson et al. | 436/127 |
| 5,650,795 | A | 7/1997 | Banno et al. | |
| 5,659,560 | A | 8/1997 | Ouchi et al. | |
| 5,699,373 | A | 12/1997 | Uchida et al. | |
| 5,751,684 | A | 5/1998 | Takeda et al. | |
| 5,764,670 | A | 6/1998 | Ouchi | |
| 5,984,868 | A * | 11/1999 | Shih et al. | 600/300 |
| 6,345,191 | B1 * | 2/2002 | Hartmann et al. | 600/310 |
| 6,599,253 | B1 * | 7/2003 | Baum et al. | 600/532 |
| 6,854,901 | B1 | 2/2005 | Ouchi | |
| 7,062,116 | B2 | 6/2006 | Ouchi | |
| 7,248,995 | B2 | 7/2007 | Itsuji et al. | |
| 7,386,024 | B2 | 6/2008 | Sekiguchi et al. | |
| 7,463,104 | B2 | 12/2008 | Sekiguchi et al. | |
| 7,557,588 | B2 | 7/2009 | Ouchi et al. | |
| 7,560,695 | B2 | 7/2009 | Kasai et al. | |
| 7,564,034 | B2 | 7/2009 | Ouchi | |
| 7,630,588 | B2 | 12/2009 | Ouchi | |
| 7,681,434 | B2 | 3/2010 | Ouchi | |
| 7,683,778 | B2 | 3/2010 | Ouchi | |
| 7,684,455 | B2 | 3/2010 | Ouchi et al. | |
| 7,688,078 | B2 | 3/2010 | Miyazaki et al. | |
| 7,689,070 | B2 | 3/2010 | Ouchi | |
| 7,701,587 | B2 | 4/2010 | Shioda et al. | |
| 7,709,797 | B2 | 5/2010 | Sekiguchi et al. | |
| 7,745,791 | B2 | 6/2010 | Kasai et al. | |
| 7,782,067 | B2 | 8/2010 | Ouchi et al. | |
| 7,869,036 | B2 | 1/2011 | Kajiki et al. | |
| 7,889,015 | B2 | 2/2011 | Sekiguchi et al. | |
| 7,922,659 | B2 | 4/2011 | Itsuji et al. | |
| 7,933,305 | B2 | 4/2011 | Ouchi et al. | |
| 7,953,130 | B2 | 5/2011 | Ouchi et al. | |
| 7,963,168 | B2 | 6/2011 | Ouchi | |
| 2003/0043379 | A1 | 3/2003 | Makino et al. | 356/437 |
| 2004/0006263 | A1 * | 1/2004 | Anderson et al. | 600/364 |
| 2007/0077176 | A1 * | 4/2007 | Lambert et al. | 422/82.05 |
| 2007/0229094 | A1 | 10/2007 | Kasai et al. | |
| 2008/0231857 | A1 * | 9/2008 | Depeursinge et al. | 356/437 |
| 2009/0198466 | A1 | 8/2009 | Kajiki et al. | |
| 2010/0140481 | A1 | 6/2010 | Ouchi | |
| 2010/0171735 | A1 | 7/2010 | Tung | |
| 2010/0252738 | A1 | 10/2010 | Kasai et al. | |

FOREIGN PATENT DOCUMENTS

| | | |
|---|---|---|
| JP | 2006-145512 A | 6/2006 |
| JP | 2008-241340 | 10/2008 |
| WO | 2006/107822 | 10/2006 |

OTHER PUBLICATIONS

International Preliminary Report on Patentability dated Jul. 7, 2011 in PCT/JP2009/071720.

* cited by examiner

ANALYSIS APPARATUS

TECHNICAL FIELD

The present invention relates to an analysis apparatus for analysis of a gas by use of a terahertz wave or an infrared ray.

BACKGROUND ART

Nondestructive sensing techniques are being developed which utilize an electromagnetic wave containing at least a part of a frequency band ranging from 30 GHz to 100 THz. Hereinafter the electromagnetic wave in this range is simply referred to as a terahertz wave. Further, analysis apparatuses are being developed which utilize an electromagnetic wave containing at least a part of a frequency band ranging from 100 THz (wavelength: 3 μm) to 430 THz (wavelength: 0.7 μm). Hereinafter the electromagnetic wave in this range is simply referred to as an infrared ray.

Japanese Patent Application Laid-Open No. 2008-241340 discloses a sensing technique with a terahertz wave for spectrometric analysis of a human exhalation air. In this technique, a substance (e.g., ethanol) in the exhaled air is aspirated into a hollow fiber and is analyzed by transmission of a terahertz wave through the substance. The aspiration is conducted for increasing the concentration of the gaseous substance in the hollow fiber.

Japanese Patent Application Laid-Open No. 2005-147962 discloses an apparatus for measuring a concentration of a gaseous substance. This apparatus collects in a cell a gas evolved from a human arm skin, and detects a transmitted light beam after multiple reflection by mirrors equipped in the cell. This apparatus is equipped with a mechanism which adsorbs the gas evolved from the arm skin with an adsorbent and desorbs the gas from the adsorbent by heating to improve the detection sensitivity.

DISCLOSURE OF THE INVENTION

The technique of Japanese Patent Application Laid-Open No. 2008-241340 requires a long time for the measurement owing to the necessary aspiration operation, and needs a long hollow fiber. On the other hand, the apparatus of Japanese Patent Application Laid-Open No. 2005-147962 requires a long time for desorption of the gas from the adsorbent by heating.

The present invention is directed to an analysis apparatus for analyzing a gas by a terahertz wave or an infrared ray comprising:
a generator for generating the terahertz wave or the infrared ray;
a trapping unit having a trapping film for trapping a gas and being capable of placing the trapping film to cause interaction between the gas trapped by the trapping film and the terahertz wave or infrared ray generated by the generator; and
a detector for detecting the interaction of the gas with the terahertz wave or infrared ray;
wherein the trapping unit comprises a structure for contact with a site evolving the gas; and
the structure is provided to hold the trapping film separately from the site.

The trapping films can be provided to trap respectively the gases selectively.

The trapping film can contain a water-repelling porous material or a hygroscopic material for trapping water vapor.

The structure can be capable of forming a space for collecting the gas to be trapped by the trapping film between the trapping film and the site, and the terahertz wave generated by the generator can transmit outside the space.

The analysis apparatus can have a waveguide for transmitting the terahertz wave or infrared ray generated by the generator, and the trapping film can be placed in the region in which the electric field of the terahertz wave or infrared ray transmitting in the waveguide is influential.

The apparatus can further comprise a reflection unit for reflecting the transmitting terahertz wave or infrared ray, and the reflection unit can be placed to reflect the transmitting terahertz wave or infrared ray plural times.

The structure can have a first flow path for introducing a gas from outside the structure, and a second flow path for discharging a gas existing between the structure and the site by the gas introduced from the first flow path.

According to the present invention, a trapping film for trapping the gas is placed separately from the gas-evolving site (e.g., a human skin), and the gas trapped by the trapping film is allowed to interact with a terahertz wave or an infrared ray generated by the generator. Thereby the gas supplied from the gas-evolving site can be analyzed effectively.

Further features of the present invention will become apparent from the following description of exemplary embodiments with reference to the attached drawings.

BEST MODE FOR CARRYING OUT THE INVENTION

The analysis apparatus for analysis of a gas by utilizing a terahertz wave or an infrared ray of the present invention is described below with reference to FIGS. 1A and 1B.

Generator 8 generates a terahertz or an infrared ray. A trapping unit is constituted of trapping film 3 and collection vessel 2. A trapping unit is provided which comprises a trapping film 3 or trapping film 4 (called also a medium occasionally; e.g., a porous polymer) and collection vessel 2. The trapping film traps a gas (e.g., a gas evolved from a human skin). The trapping unit is placed to cause interaction between the trapped gas and the terahertz wave or the infrared ray generated by generator 8. Detector 10 detects the terahertz wave or infrared ray which has interacted. The trapping unit contains structure (collection vessel) 2 which is brought into contact with the gas-evolving site 1 (e.g., a portion of a human body like an arm or a hand). The structure 2 serves to keep the trapping film 3 separately from the site 1 not to come into contact. Thereby the gas evolved from the site 1 can be analyzed effectively in a short time.

The structure 2 is also called as "spacer" and serves for providing a specific space between the trapping film 3 and the site 1. The structure is preferably made of a resin etc. and preferably has a shape of cap as shown in FIG. 1A or a shape of a bag as in FIG. 1B.

The trapping films 3, 4 are preferably provided to trap respectively different gases (e.g., ammonia and acetone contained in the skin gas). The trapping films 3, 4 are preferably laminated together (see description with reference to FIGS. 3A and 3B).

The trapping film preferably has a water-repelling porous material beside the gas-trapping film for trapping the gas. Otherwise, the trapping film preferably contains a hygroscopic material (e.g., silica gel). This is because water in the gas absorbs the terahertz wave, and water vapor contained additionally in the gas trapped by the trapping film will interfere the effective analysis.

Structure 2 is preferably constituted so as to provide a space for collecting the gas to be trapped by trapping film 3 between trapping film 3 and the site 1. With this structure, the terahertz wave generated by generator 8 is allowed to propagate outside the space. The apparatus and method of this embodiment are described below.

That is, the medium for trapping the gas molecules is placed in the space adjacent to the gas molecule-evolving site (e.g., human skin) separately from the gas molecule-supplying site and in the region where the electric field of the propagating terahertz wave is influential. Thereby the detector detects the terahertz wave transmitting through at least a part of the trapping unit having the medium.

According to the above principle, the apparatus and method of the present invention is basically constituted as below. The detection apparatus for detection of information of the gas molecules (kind, concentration, etc.) comprises a trapping unit in a shape of a vessel, a medium in a plate or a like shape for trapping the gas molecules to be detected, a generator for generating the terahertz wave, and a detector. At least a part of the collection unit is brought into contact with a part of the human body evolving the gas molecules to be detected to form a space for collection of the gas molecules. The detector detects the terahertz wave transmitting through at least a part of the medium in the collection unit. The medium is placed in the space in the collection unit separately from the gas-molecule-evolving site, and in the region where the propagating terahertz is influential.

Thereby, the space in the collection unit for placing the medium can be made smaller, and the system can be made smaller for detecting information such as the kind and concentration of the component of the gas molecules evolved from the gas evolving site. Further, since the gas molecule information is detected by detecting the terahertz wave transmitting a part of the medium placed in the space in the collection unit, the information can be detected at a relatively high speed. Therefore, for example, a human health state can be diagnosed noninvasively by high-speed detection of the component in an exhaled gas or a skin gas.

Further, the skin-gas detection apparatus for detection of information on gas molecules of the human skin gas has a hygroscopic material in the collection unit for trapping water molecules. In this embodiment also, the collection unit has an interspace for collecting the gas molecules with at least a part of the medium in the collection unit in contact with at least one of the human skin evolving the gas molecules to be detected. The detector detects the terahertz wave transmitted from the generator through at least a part of the medium in the collection unit. The medium is placed in the space of the collection unit and apart from the human skin and in the region where the transmitted terahertz wave is influential.

In the scope of the above basic embodiment, specific examples mentioned below are practicable. The collection unit may be placed in a part of the terahertz wave transmission region between the generator and the detector. Plural kinds of the mediums may be provided in the region where the electric field of the hertz wave is influential. The plural kinds of the mediums may be laminated together (e.g., trapping films 3 and 4 in FIGS. 1A and 1B).

In the space in the collection unit, a hygroscopic material may be provided additionally for trapping the water molecules. The hygroscopic material may constitute a part of the laminated medium (e.g., trapping film 51 in FIG. 4A). Such a constitution is applicable suitably as a skin gas detector. The medium for trapping the gas molecules may be constituted from a water-repellent porous material.

The medium for trapping the gas molecules may be constituted from a member capable of trapping selectively gas molecules to be detected. The selective trapping members of plural kinds may be placed in the region where the terahertz wave is influential. The plural pieces of the information can be detected by the individual medium independently for the respective kinds of the gas molecules.

Figure 4A:
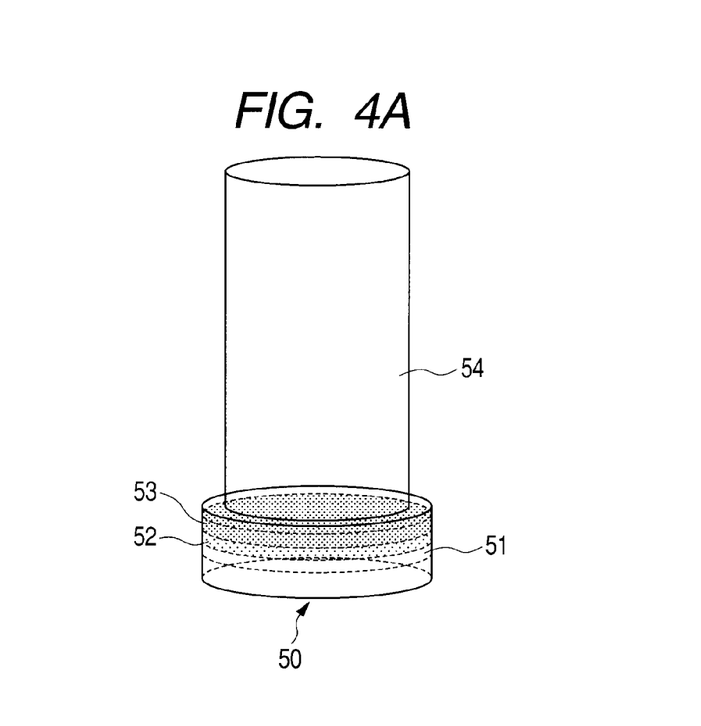
FIGS. 4A and 4B are schematic drawings for describing an example of the present invention.
Figure 4B:
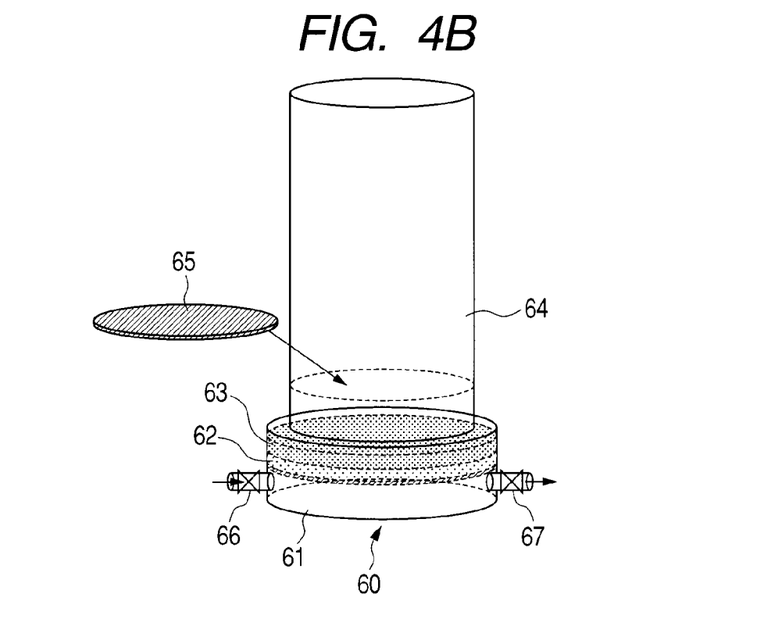
Figure 5A:
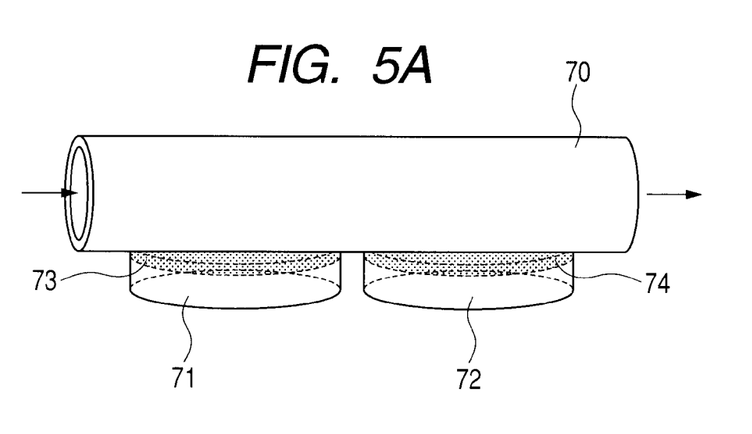
FIGS. 5A, 5B and 5C are schematic drawings for describing an example of the present invention.
Figure 5B:
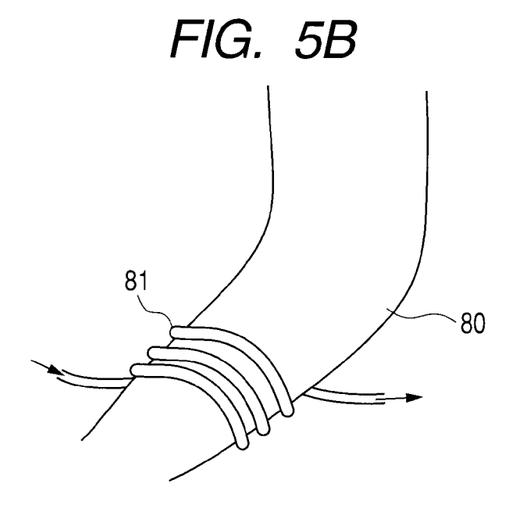
Figure 5C:
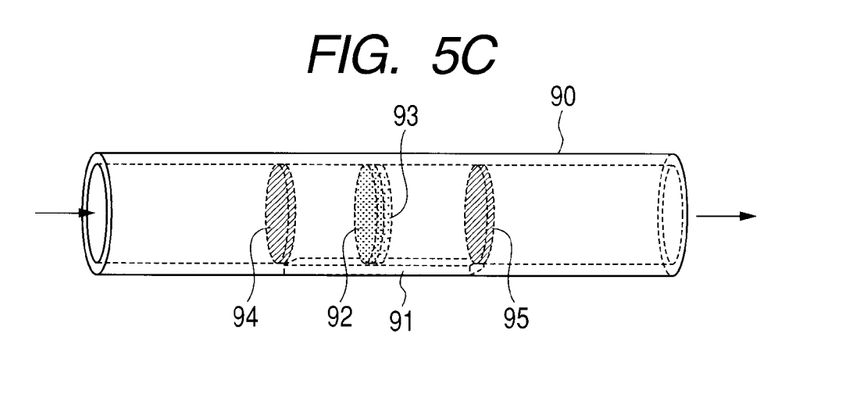

In another embodiment, a reflection member like a metal mesh for multiple reflection of the terahertz wave may be additionally provided to detect a terahertz wave which has transmitted several times through at least a part of the gas-trapping medium (e.g., mirrors 62 and 65 in FIG. 4B, and mirrors 94 and 95 in FIG. 5C). The suitable reflection unit has openings like a metal mesh and capable of passing the gas molecules to be detected.

The apparatus has preferably a waveguide for transmitting the terahertz wave or infrared ray generated by the generator. With the waveguide, the trapping film is preferably placed in the region where the electric field of the terahertz wave or infrared ray passing through the waveguide is influential, like waveguide 70 in FIG. 5A and waveguide 90 in FIG. 5C. Naturally, the analysis apparatus may be constituted so as to transmit the terahertz wave or infrared ray generated by the generator through the space.

Further, the waveguide contains preferably a reflection member (e.g., the above-mentioned metal mesh) for reflecting the terahertz wave or infrared ray transmitting through the waveguide. The reflection member is preferably placed to reflect several times the terahertz wave or infrared ray transmitting through the waveguide.

A means for purging the space in the collection unit may be provided additionally. The purging means is exemplified by first flow channel 66 in FIG. 4B provided in the structure to introduce a gas from the outside into the structure; and second flow channel 67 for discharging the gas accumulated between the structure and the site by introduction of a gas through first flow channel 66.

(Reflection Type Analysis Apparatus)

In this embodiment, the above embodiment is described with reference to FIG. 1A.

The gas-molecule-evolving site 1 is a part of human arm. Vessel 2 of collection unit for collecting the gas molecules evolved from gas molecule-evolving site 1 is formed from a resin or a like material. In FIG. 1A, the constitution of vessel 2 is illustrated perspectively for ease of understanding.

Film-shaped mediums 3 and 4 laminated are placed near the top face of collection vessel 2 for trapping the gas molecules and apart from the gas-molecule-evolving site. Trapping films 3, 4 are preferably made, for example, of a polymer which causes less the loss of the terahertz wave. The preferred polymer includes polyethersufone, nylon, polypropylene, polysulfone, Tefron®, polyolefin, polyethylene, polystyrene, and tetrafluoroethylene. The pores in trapping films 3, 4 has an average diameter of preferably not larger than several ten μm, which is much smaller than the terahertz wave length, more preferably less than several μm. The film of such a constitution functions usually as a scattering body to light of a conventional sensing means and cannot be used for sensing uses. Incidentally, the present invention uses at least either one of trapping films 3 and 4.

Collection vessel 2 has an opening on the side of gas-molecule-evolving site 1 (bottom side), and is attached closely at the top side to path 5 for transmission of terahertz wave 6. The gas molecules from gas-molecule-evolving site 1 are collected into collection vessel 2 having a nearly completely closed space for the gas molecules for concentration and are trapped by trapping films 3 and 4. The isolation of the trapping film and gas-molecule-evolving site 1 in collection vessel 2 enables decrease of direct adherence of undesired molecules from gas-molecule-evolving site 1 such as water vapor, a component contained in sweat, and skin-adhering substance. Trapping films 3, 4 are constituted respectively from a porous polymer having a small average pore size as mentioned above to prevent leakage of the gas molecules from collection vessel 2.

Terahertz wave 6 generated by generator 8 is transmitted through half mirror 7 and transmission path 5 to trapping films 3 and 4. The wave reflected by trapping films 3, 4 is transmitted again backward through transmission path 5 and reflected by half mirror 7 and introduced to detector 10. Preferred half mirror 7 includes a high-resistance silicon substrate, and a metal mesh structure.

Controlling-processing assembly 9 controls generator 8 and detector 10, and analyzes information on the kind and concentration and other properties of the trapped gas molecules trapped by trapping films 3, 4. The controlling-processing assembly may be separated for the functions or may be constituted in integration. The two kinds of trapping films 3 and 4 may be designed to trap respectively selectively different gas molecules. The gas molecule to be detected includes alcohol, acetaldehyde, acetone, and ammonia, but is not limited thereto.

(Terahertz Time Domain Spectroscopy)

Figure 2:
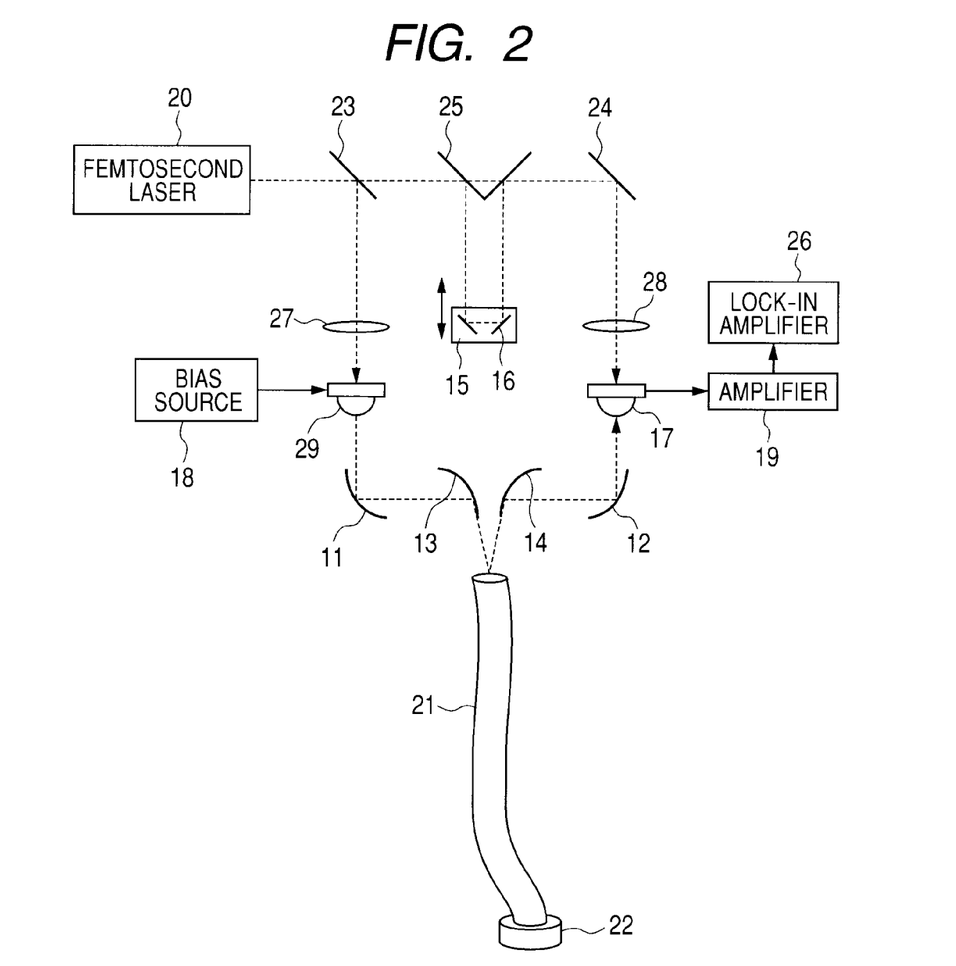
FIG. 2 is a schematic drawing for describing an example of the present invention.

Next, a terahertz time domain spectroscopy, which is a usual apparatus for a terahertz wave, is described with reference to FIG. 2.

The laser beam having a pulse width of less than 100 fsec emitted from femtosecond laser 20 is branched into two branched beams by half-mirror 23. One branched beam is condensed by lens 27 and is projected to photoconductive element 29 constituting a generator. The bias voltage applied to this photoconductive element 29 is modulated by power source 18. The modulated terahertz wave is introduced by parabolic mirrors 11, 13 to terahertz waveguide 21. Otherwise, the terahertz wave may be introduced directly to the trapping film.

The other branched laser beam is transmitted through mirror 25 to mirror pair 16 of delay stage 15, where the laser beam is delay-controlled, and transmitted via mirrors 25, 24 and lens 28 to photoconductive element 17 constituting the detector.

Waveguide 21 for the terahertz wave may be formed from a material such as a hollow fiber having a metal coat inside, a photonic crystal fiber having a periodical hole structure, a metal single wire, a waveguide tube, a two-conductor wire like a coaxial line or a balanced line, and those coated with a resin. Otherwise, the terahertz wave guide may be a hard tubular fiber capable of transmitting the terahertz wave in a beam as it is. To the front end of fiber 21, collection vessel 22 is connected which has the aforementioned trapping film built therein and constitutes the collection unit. In the analysis operation, the collection vessel is pressed against the measurement site in a manner as an auscultator to form a space for collecting the evolved gas molecules. The measurement site includes a gas-molecule-evolving site such as a portion of a human skin, a mouth, and a nose, and a gas molecule-evolving place such as the earth surface, and production fields. The terahertz wave transmitted through fiber 21 is introduced to the trapping film (not shown in FIG. 2) in collection vessel 22. The terahertz wave is reflected by the film, transmitted through fiber 21 again and parabolic mirrors 14, 12, and is detected by photoconductive eminent 17. In this embodiment, the introduction and emission of the terahertz wave is conducted by two parabolic mirrors 13, 14 spatially, not by the half mirror. Instead, the laser beam may be branched by half mirror 7 (e.g., a metal wire). The signal of the terahertz wave is detected through amplifier 19 and lock-in amplifier 26 in a synchronous detection manner and is analyzed by processing unit 9.

Figure 3A:
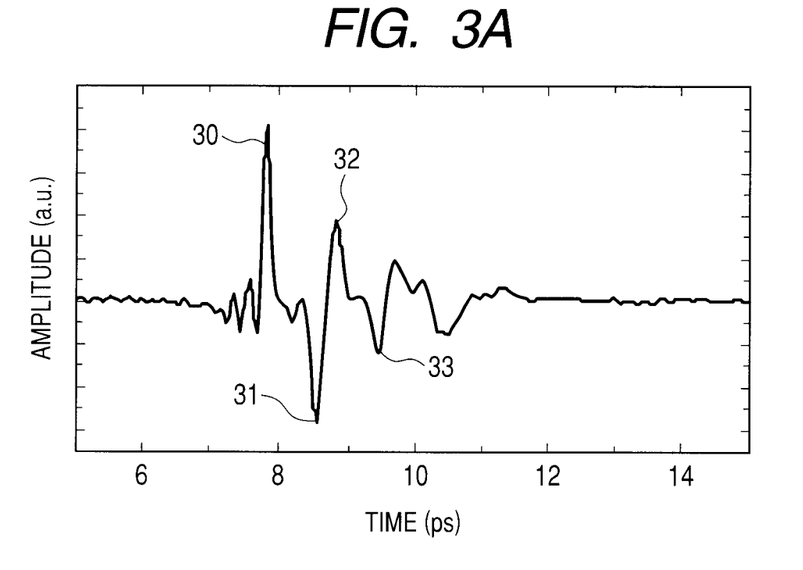
FIGS. 3A and 3B are schematic drawings for describing an example of the present invention.

FIG. 3A shows an example of the analyzed temporal waveform. Reflection pulses from the interfaces of laminated trapping films are shown. The numerals 30, 31 denote reflection pulses from the front face and back face of the first film (trapping film 4 in FIGS. 1A and 1B), and the numerals 32, 33 denote reflection pulses from the front face and back face of the second film (trapping film 3 in FIGS. 1A and 1B). The information on the gas molecules trapped by the respective trapping film can be derived from the positions and lengths of the trapping films through which the pulses penetrate. This is because the trapping films in this embodiment allow penetration of the terahertz wave and the reflected positions can be estimated from the signals of the terahertz wave reflected at the interfaces.

Figure 3B:
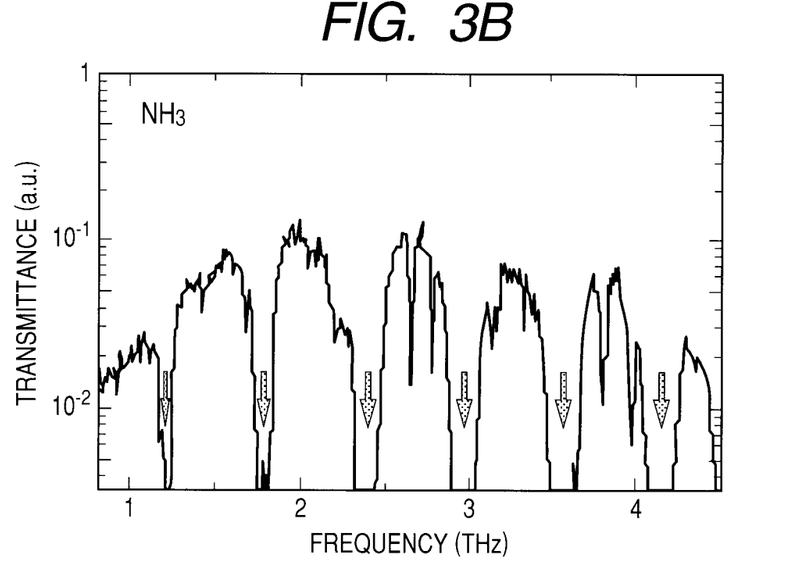

For example, FIG. 3B shows a spectrum of ammonia. The properties and concentration of the ammonia can be estimated from the intensity and position of the absorption frequency of the reflected pulses from the front face and back face of the one film. By the other film, acetone, for example, may be trapped, and information of plural kinds of gas molecules can be derived. By such a multilayer structure, plural pieces of information can be estimated simultaneously. Naturally one kind of gas molecules may be detected by use of a single trapping film.

(Solubility Parameter)

In this embodiment, the trapping film is capable preferably of trapping selectively an objective gas. For this purpose, the solubility parameter of the trapping film is selected to be approximate to the solubility parameter of the gas to be trapped for the higher affinity between the film and the gas. The solubility parameter is a parameter for indicating affinity between substances. The closer the solubility parameters of substances, the higher is the affinity between the substances. Therefore, the trapping film having the solubility parameter close to that of the gas will trap the gas selectively.

For example, a gas of acetone having a solubility parameter of $10.0\,[(cal/cm^3)^{1/2}]$ can readily be trapped by a trapping film made of cellulose acetate having a solubility parameter of $10.9\,[(cal/cm^3)^{1/2}]$, and made of polyether sulfone having a solubility parameter of $9.7\,[(cal/cm^3)^{1/2}]$. In contrast, the acetone gas is not readily trapped by the trapping film made of polystyrene having a solubility parameter of $9.0\,[(cal/cm^3)^{1/2}]$. The gas of ammonia having a solubility parameter of about $15\,[(cal/cm^3)^{1/2}]$ is readily trapped by the trapping film made of polyvinyl carboxylate ester having a solubility parameter of $15.8\,[(cal/cm^3)^{1/2}]$, and polyvinylpyrrolidone having a solubility parameter of $15.8\,[(cal/cm^3)^{1/2}]$. The gas of ethanol having a solubility parameter of $12.9\,[(cal/cm^3)^{1/2}]$ is readily trapped by a trapping film made of polyester having a solubility parameter of $12.5\,[(cal/cm^3)^{1/2}]$, and ABS resin having a solubility parameter of $12.8\,[(cal/cm^3)^{1/2}]$.

The method of preparation of the trapping film is not limited insofar as an intended solubility parameter can be obtained. For example, the solubility parameter of the surface of a trapping film may be changed by ozone treatment or other surface modification treatment. Otherwise a certain liquid or gas may be allowed to infiltrate into the trapping film preliminarily. Further, in the present invention, the trapped gas may be allowed to react with the trapping film and the reaction product may be subjected to the spectral measurement of the gas.

With the detection apparatus of this embodiment, the gas is trapped by the trapping film, and simultaneously the state is sensed by a terahertz wave. Therefore, the information on the gas molecules can be obtained in several minutes. A health state or the like can be speedily diagnosed from the information on the evolved gas molecules without load to the human body. The high speed diagnosis enables observation of temporal variation of the measurement results, or simultaneous measurement at several sites by real-time measurement. This enables a novel method for detection of gas molecules, and a novel diagnosis method employing the detection method.

(Transmission Type of Analysis Apparatus)

Another embodiment is described below with reference to FIG. 5A. In this embodiment, the generation and detection is conducted with a transmission arrangement, not with a reflection arrangement. In FIG. 5A, the waveguide 70 for the terahertz wave is a hollow fiber made of a resin as mentioned before. Collection vessels 71, 72 have respectively a trapping film 73 or 74 and are fixed to fiber wave guide 70. At the portions where the respective collection vessels are fixed, the thickness of the resin of fiber waveguide 70 is made thinner. Collection vessels 71, 72 are placed in such positions that the terahertz wave transmitting through the waveguide 70 diffuses to cause interaction with trapping films 73, 74.

This embodiment of a transmission arrangement does not use half mirror 7. In FIG. 5A, the terahertz wave is transmitted in the arrow direction, and the generator is placed at the left side, and the detector is placed at the right side (not shown in FIG. 5A).

In this embodiment, it is difficult to make the trapping film in multiple layers, but instead, plural collection vessels can be placed in the terahertz wave transmission direction. In this arrangement, the same one kind of gas molecules can be detected or different gas molecules can be detected. Plural kinds of gas molecules different in absorption spectrum frequency can be detected respectively separately. In time domain spectrometry, superposed signals of the gas molecules are obtained. Therefrom information of plural kinds of gas molecules can be obtained simultaneously by spectral analysis after Fourier transformation.

In another method, plural single-frequency light sources are provided in correspondence with the absorption wavelengths of the respective gas molecules, the plural frequencies of terahertz waves are allowed to transmit in the same one waveguide, and the terahertz waves are separated by filters at the detection side to obtain information on the gas molecules to be detected.

In still another method, to increase the interaction between the trapping film and the terahertz wave, a resonator is constituted by placing two metal meshes in waveguide 70 as the reflection members as illustrated in FIG. 4B. With the terahertz pulse, the sensitivity can be raised by collecting information from a plurality of pulse trains.

The waveguide fiber made from a flexible material for the terahertz wave transmission can be used for measurement at the gas-molecule-evolving site in a tubular shape like human arm 80 by winding the fiber waveguide 81 around the measurement site as illustrated in FIG. 5B. In FIG. 5B the arrow marks indicate the terahertz wave transmission direction. Naturally this direction may be reversed. In other respects, the constitution is the same as the above embodiment.

(Analysis Method)

The method for analysis of a gas by use of a terahertz wave or an infrared ray comprises the steps (a) to (c) below:

(a) a trapping step for trapping a gas;
(b) a generating step for generating a terahertz wave or an infrared ray; and
(c) a detecting step for detecting the trapped gas by interaction of the trapped gas with the generated terahertz wave or infrared ray, and measurement of the terahertz wave or infrared ray which has interacted.

Further, the method may comprise a positioning step for placing a collection unit having a medium for trapping the gas molecules to be detected and a space for collecting the gas molecules so as to be in contact with at least a part of the site (e.g., a part of a human body) evolving the gas molecules to be detected. The method may comprise also a transmitting step for transmitting the terahertz wave through at least a part of the medium in the collection unit. The method may comprise also another detecting step for detecting the terahertz wave transmitted through at least a part of the medium in the collection unit. In the positioning step, the medium is positioned in the space in the collection unit to be isolated from the gas-molecule-evolving site and in the region where the terahertz wave is influential.

In the above analysis method, for example, the site evolving the gas molecules to be detected is a part of a human body, and the collection unit is brought into contact with the part of the human body to detect information on the gas molecules evolved from the human body. Information on gas molecules evolved from the human body can be detected by winding a flexible waveguide such as an optical fiber around a measurement position of the human body such as a skin. Thus from the information on the detected gas molecules, a human disease can be diagnosed.

Further, the present invention can be practiced by conducting the processing treatment below. A software program is installed from a network or a memory medium, and the system or computer of the apparatus (or CPU, or MPU) reads out the program and practice it. Any memory medium may be used insofar as it is capable of storing the program for driving the computer.

EXAMPLES

Specific examples of the present invention are described below.

First Example

This Example is described with reference to FIG. 1A and FIG. 2. Femtosecond laser 20 is a fiber laser of a wavelength of 1.55 μm and a pulse width of 20 fsec. The generator element and detector element of the terahertz wave were respectively a Be-doped low-temperature-grown InGaAs having a dipole antenna. A laser beam of 10 mW was projected to the generator side and a laser beam of 5 mW was projected to the detector side.

Further, a modulation signal of ±10V of a rectangular wave of 50 KHz as the bias voltage was applied to the generator side, and the output of current-voltage transformation amplifier 19 of a gain of $10^7$ was synchronously detected by lock-in amplifier 26 to obtain a detection signal of a high S/N ratio. At the detection side, a photoconductive element formed from low-temperature-grown GaAs which causes a less dark current was used for improvement of the S/N ratio, since InGaAs can not always give sufficient S/N ratio. With this constitution, the laser beam projected to the detector side has preferably a wavelength longer than the band gap of the GaAs. Therefore in this case, the wavelength is converted to a double wave of 780 nm by a second harmonic generation element (not shown in the drawing) like periodically poled ithium niobate (PPLN) and is projected to the GaAs photoconductive element. Instead, in this case the GaAs may be excited directly by a pulse beam of 1.55 μm without generating the second harmonic wave. In the generator side, an organic nonlinear crystal (e.g., DSAT: 4-dimethylamino-N-methyl-4-stilbazolium) tosylate can be used for measurement in the band range up to 100 THz.

In this Example, a hollow waveguide was used as the waveguide 21 of the terahertz wave. A collection vessel 22 made of a resin was attached to the front end of hollow waveguide 21 for operation of the terahertz-reflection type time domain spectrometer. This collection vessel 22 may be detachable from waveguide 21.

FIG. 4A illustrates the construction of the collection vessel used in this Example. Three trapping films 51, 52, and 53 are employed in this Example, but are not limited thereto. Two trapping films may be employed as illustrated in FIG. 1A, or a single trapping film may be employed. In this Example, first trapping film 51 is a hygroscopic film comprising silica gel or the like to adsorb water molecules evolved from the human body other than the gas molecules to be detected. This hygroscopic film prevents water condensation caused by rise of water vapor pressure in collection vessel 50 and adhesion of water vapor onto trapping films 52, 53. Further, this hygroscopic film serves to prevent loss in the terahertz wave transmission by water vapor filled in waveguide for the terahertz wave or to exclude a noise of the water molecule spectrum. First trapping film 51 may be a film having a function other than the hygroscopic film, and may serve as a water-repellent porous film which intercepts the passage of water molecules but allows other molecules to pass through. Otherwise, a hygroscopic agent may be placed at any position in collection vessel 50.

Second trapping film 52 may be made of a porous material constituted of a polyether-sulfone for selective trapping of acetone. Third trapping film 53 may be made of a porous material constituted of a polyvinylpyrrolidone for trapping of ammonia. In this case, in the reflection echo pulse in FIG. 3A, the numeral 30 denotes the reflection pulse at the front face of third trapping film 53, and the numeral 31 denotes the reflection pulse at the back face (gas molecule evolution side) of third trapping film 53. The numeral 32 denotes the reflection pulse at the front face of second trapping film 52. Therefrom, the amount of ammonia adsorbed by third trapping film 53 can be estimated since the pulses 31 and 32 represent the terahertz waves which have passed through third trapping film 53. Similarly the numeral 33 denotes the reflection pulse at the back face of second trapping film 52. Therefore information on acetone can be obtained in consideration of the information on the ammonia. The succeeding echo pulses contain information from hygroscopic film 51 as well as information from other films since the terahertz wave passes through the films and contains information from the respective films. Therefore, the information in the respective films can be obtained from the plural pulse waveforms by calculation. The calculation can be conducted by increasing the S/N ratio by signal processing technique by deconvolution or wavelet transformation.

On the other hand, the ammonia evolved from the human skin is known to correlate with cancer, hepatocirrhosis, helicobacter pylori, uremia, and like diseases. The acetone evolved is known to correlate with diabetes, autointoxication, obesity, and the like diseases. Therefore, the health state of a man or woman can be diagnosed by the apparatus and method of the present invention. The apparatus and method of the present invention is different from conventional diagnosis in which the gas molecules are aspirated and adsorbed and the adsorbed gas molecules are determined after lapse of a prescribed time. In contrast, in the present invention, the information on the evolved gas molecules can be obtained at any time during trapping of the gas molecules by the trapping films without giving a pain to objective person at a high speed.

The kind of the gas molecules to be detected is not limited to the above-mentioned ones, but includes gas molecules having correlation with diseases. For example, methane, ethane, ethylene, aldehydes, ethanol, and nitrogen monoxide are evolved from the human skin. Nitrogen monoxide has correlation with cardiovascular diseases. Otherwise, this embodiment is similar to the embodiment described before with reference to FIGS. 1A and 2.

Second Example

This Example is a modification of the embodiment of First Example in which broad band spectrometry is conducted with terahertz pulses. For measurement of absorption of only a specified kind of molecules at a specified frequency, a single-frequency oscillator may be used as the generator or the light source.

Figure 1A:
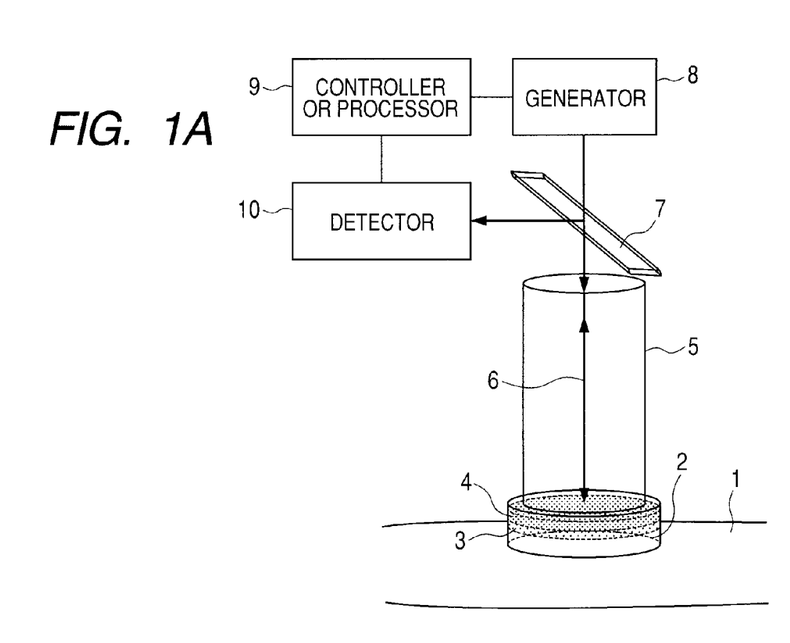
FIGS. 1A and 1B are schematic drawings for describing an example of the present invention.
Figure 1B:
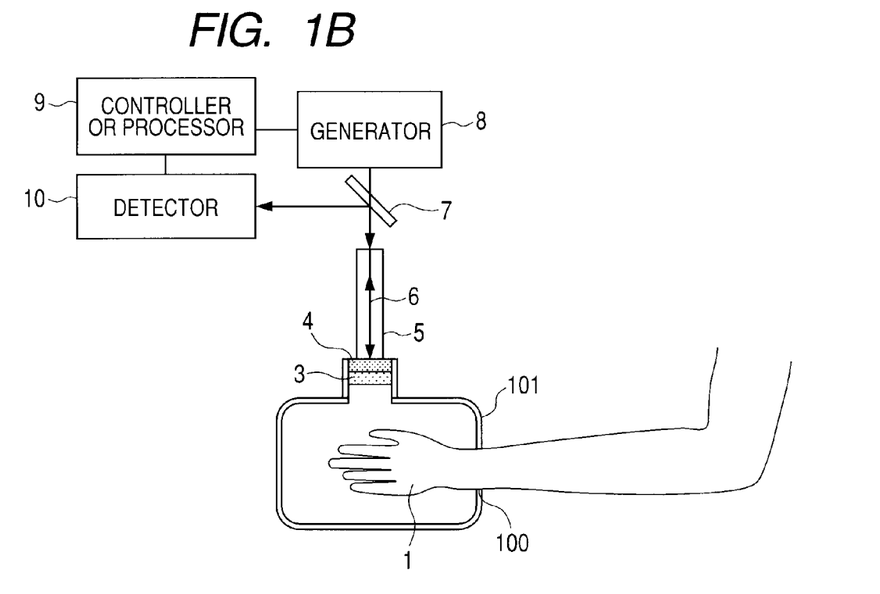

In this Example, a current injection type oscillator is employed as generator 8 in FIG. 1A, including a semiconductor laser, a quantum cascade laser, and a resonance tunnel diode oscillator. The semiconductor laser is capable of generating an electromagnetic wave in the near-infrared frequency band ranging from 0.7 μm to 2 μm. The quantum cascade laser covers the range from about 1 THz to 150 THz, and the resonance tunnel diode covers fragmentally the range from 0.1 THz to 1 THz. One or more elements are employed as the generator in accordance with the characteristic spectrum of the gas molecules to be detected, and a generated beam is projected to the trapping film of the collection unit. When a near-infrared ray is employed, the trapping film should be a filter having a fine structure in order to prevent light scattering. In this case, the useful film includes a polytetrafluoroethylene film (pore size: 0.1 μm), and a polycarbonate film (pore size: 0.05 μm, 0.1 μm). The terahertz wave generator is exemplified by the one which projects beams from two laser diodes to a single carrier photodiode to generate a terahertz wave corresponding to the difference frequency of the two laser beams. Other examples of the terahertz generator include a Josephson element, and a gas laser. The reflected wave is detected by terahertz detector 10 such as a bolometer, a pyro element, a Schottky-barrier diode, and a quantum effect element (QWIP). When a near-infrared ray is employed, a pin photo-diode for optical communication, an avalanche photodiode, and an MSM type detector are useful.

In measurement by changing the oscillation frequency of the terahertz wave of the terahertz generator, the detection signal can be obtained from terahertz wave detector 10 while controlling the change by controlling-processing assembly. In this measurement, the information on the gas molecules can be obtained by processing the data as spectral information in a specific range, for example, in a width of several tens of GHz.

With the light source of such a narrow frequency range, a narrow-band terahertz fiber is useful as the waveguide. For example, a porous fiber made from polyvinylidene fluoride (PBDF). The material of the waveguide is selected from those causing less a loss of the terahertz wave, including Teflon®, polyolefin, polyethylene, and PMMA. Photonic crystal fibers are useful also. In a broad band range, a hollow fiber is useful. In communication wavelength band, general-purpose quartz and plastic optical fibers are useful.

According to this Example, a change in the detection signal at a specified frequency can be detected at a high sensitivity. Therefore, a gas component having a known spectrum can be detected in a micro-quantity. By use of a current-injection type of terahertz wave generator, the entire apparatus can be made further smaller than the one in First Example.

Third Example

In the above Examples, only the terahertz wave reflected by the trapping film is detected as the signal component. In this Third Example, the terahertz wave which is not reflected by the trapping film but penetrates through the film is utilized effectively. The terahertz wave can be reflected by a metal wire mesh. Therefore, metal mesh mirror 62 is placed between trapping film 63 and intake opening 61 of collection vessel 60 as illustrated in FIG. 4B to reflect the terahertz wave which has penetrated through trapping film 63 to pass trapping film 63 again to reach the detector.

With this constitution with a terahertz wave pulse, the echo pulse train as shown in FIG. 3A is repeated after the peak 33 (not shown in the drawing). The detection sensibility can be increased by integration of plural pulses containing the information from trapping film 63 in consideration of the position of metal mesh 62 and the time-position.

As metal mesh mirror 62, a square mesh of 250 µm of tungsten wire has a reflective index of nearly 100% in a wavelength range of higher than 0.8 THz, whereby the length of the interaction between the terahertz wave and trapping film 63 is increased. By use of a metal mesh having an opening, the gas molecules to be trapped are allowed to pass through the mesh to be adsorbed by trapping film 63. A fraction of the gas molecules can adhere to the metal mesh. This adhesion of the gas molecules to the metal mesh can be prevented by coating or providing a heater or a like mechanism. When the terahertz wave is polarized, the reflection mirror may be constituted of a wire grid.

A second metal mesh mirror 65 may be provided additionally at the position indicated by a dotted line in the side of terahertz waveguide 64 to form a resonator. Mirror 65 on the waveguide 64 is designed to have a reflection index lower than that of metal mesh 62 to increase the quantity of the signal to the detector side. The pulse reflected by metal mesh mirror 65 may be utilized as the reference waveform in signal processing like deconvolution. Otherwise, in place of the mesh having openings, a mirror having no opening, for example, a resin plate coated with gold in a nanometer order, or a dielectric multiple-layered mirror is used as mirror 65 to improve the air-tightness in the collection vessel 60.

When the resonator constituted of metal mesh 62 and mirror 65 has a resonator length of 1.5 mm, the terahertz wave reciprocates in a time of $2 \times 1.5$ mm/$3 \times 10^8$ m=10 psec (refractive index of trapping film 63 being assumed to be 1). Therefore, the terahertz pulse having a pulse width of 300 fsec is observed every 10 psec. Actually, however, since the refractive index of trapping film 63 is higher than 1, the reciprocation time is longer depending on the thickness thereof, and the pulses reflected at the front and back faces of the trapping film 63 are observed between the reflection pulses from the faces of mirrors 62, 65. From the detected pulses, the information on the gas molecules adsorbed by trapping film 63 is detected at a high sensitivity by integration in the same manner as above.

Trapping film 63 and metal mirrors 62, 65 may be placed separately from each other, or in close contact with each other.

In this Example, a purging mechanism may be provided which purges the inside of collection vessel 60 with another gas. Specifically, valved first flow path 66 and valved second flow path 67 are equipped employed for introducing and discharging the purge gas. With this mechanism, after collection vessel 60 is placed at a prescribed position, an inside gas can be replaced by introduction of nitrogen or a like gas. Otherwise, the inside of collection vessel 60 may be evacuated. The nitrogen purge or evacuation of the collection vessel 60 increases the sensitivity of detection of the objective molecules. The nitrogen purge or the evacuation enables removal of an unwanted substance adhering to metal mesh mirror 62.

Fourth Example

This Fourth Example of the present invention is a modification of the embodiment illustrated in FIG. 5A. In this Example, as illustrated in FIG. 5C, trapping films 92, 93 are placed inside hollow terahertz waveguide 90. With this constitution, a resonator is formed by a pair of mirrors 94, 95 as in Third Embodiment, and the terahertz wave transmitting thorough trapping films 92, 93 is detected. When the gas molecules to be detected are present in a sufficiently high concentration, the resonator need not be formed.

Intake opening 91 for introducing the gas molecules is formed by boring a part of the wall of waveguide 90 for introducing the gas molecules into waveguide 90 through intake opening 91. Mirrors 94, 95, which are constituted from a material not permeable to the gas molecules, make the resonator in the collection vessel air-tight. Mirrors 94, 95 may be constituted of a fine mesh of a metal.

The entire constitution of the measurement apparatus and the measurement method are similar to those mentioned in the embodiment of the preceding Examples. With waveguide 90 made of a flexible fiber, the waveguide may be wound around the gas molecule-evolving site for the measurement as illustrated in FIG. 5B.

The length of intake opening 91 need not be made equal to the length of the resonator. Reflection mirror 94, 95 may be brought into close contact with trapping films 92, 93, while partition walls are formed from a resin or a like material, the partition walls making the collection vessel air-tight but allowing the terahertz wave to penetrate.

In this Example, the collection vessel, and trapping films 92, 93 may be included inside waveguide 90 (that is, the collection unit is constituted by a part of waveguide 90) to make smaller the detection apparatus.

Fifth Example

This Example is a modification of a spectral system for terahertz waves of First Example. This Example uses a collection unit enlarged to enclose a wrist and hand as illustrated in FIG. 1B. Contact portion 100 between the wrist and collection vessel 101 is closed not to allow the environmental air to flow into collection vessel 101 in a large amount. Collection vessel 101 is not limited in the material and the shape.

The inside wall face of collection vessel 101 may be covered with a fluorine compound like Teflon, or a metal like stainless steel and aluminum.

Collection vessel 101 may have a gas inlet and a gas outlet for introducing and discharging a carrier gas like nitrogen (e.g., gas flow channels 66, 67 in FIG. 4B). The flow of the carrier gas can prevent water adhesion or dew condensation on the inner wall of collection vessel 101 in collection of the sample gas. Collection vessel 101 of this Example enables collection of the sample gas from a larger site to increase the analysis accuracy and the kinds of the gas detected.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-331601, filed Dec. 25, 2008, and Japanese Patent Application No. 2009-265226, filed Nov. 20, 2009, which are hereby incorporated by reference herein in their entirety.

The invention claimed is:

1. An apparatus for time domain spectroscopy comprising:
a generator for generating a pulsed terahertz wave or an infrared ray;
a trapping unit including first and second trapping films and being capable of placing the first and second trapping films such that the first trapping film is irradiated with the terahertz wave or infrared ray generated by the generator and the second trapping film is irradiated with the terahertz wave or infrared ray transmitted through the first trapping film;
a detector for detecting the terahertz wave or infrared ray which has interacted with a first gas which has been trapped by the first trapping film and a second gas which has been trapped by the second trapping film, wherein the second gas is different from the first gas; and
a processing unit for obtaining a temporal waveform from a detection result of the detector and for obtaining information on types or properties of the first and second gases;
wherein the trapping unit comprises a structure for contact with a site evolving the gas,
wherein the structure is provided to hold the trapping films separately from the site, and
wherein the processing unit obtains information on the first gas based on a pulse from the first trapping film in the temporal waveform and obtains information on the second gas based on a pulse from the second trapping film in the temporal waveform.

2. The analysis apparatus according to claim 1, wherein a part of the trapping films contain a water-repelling porous material or a hygroscopic material for trapping water vapor.

3. The analysis apparatus according to claim 1, wherein the structure is capable of forming a space for collecting the gas to be trapped by the trapping films between the trapping films and the site, and the terahertz wave generated by the generator transmits outside the space.

4. The analysis apparatus according to claim 1, wherein the analysis apparatus has a waveguide for transmitting the terahertz wave or infrared ray generated by the generator, and the trapping films are placed in the region in which the electric field of the terahertz wave or infrared ray transmitting in the waveguide is influential.

5. The analysis apparatus according to claim 3, which further comprises a reflection unit for reflecting the transmitting terahertz wave or infrared ray, and the reflection unit is placed to reflect the transmitting terahertz wave or infrared ray plural times.

6. The analysis apparatus according to claim 1, wherein the structure has a first flow path for introducing a gas from outside the structure, and a second flow path for discharging a gas existing between the structure and the site by the gas introduced from the first flow path.

7. The analysis apparatus according to claim 1, further comprising:
a film positioned between the trapping films and the site, which film contains a water-repelling material or a hygroscopic material.

* * * * *